United States Patent
Kumar

(10) Patent No.: US 11,440,959 B2
(45) Date of Patent: Sep. 13, 2022

(54) CD226 AGONIST ANTIBODIES

(71) Applicant: Eli Lilly and Company, Indianapolis, IN (US)

(72) Inventor: Naresh Kumar, Hawthorne, NY (US)

(73) Assignee: Eli Lilly and Company, Indianapolis, IN (US)

( * ) Notice: Subject to any disclaimer, the term of this patent is extended or adjusted under 35 U.S.C. 154(b) by 337 days.

(21) Appl. No.: 16/500,947

(22) PCT Filed: Jul. 19, 2019

(86) PCT No.: PCT/US2019/042604
§ 371 (c)(1),
(2) Date: Oct. 4, 2019

(87) PCT Pub. No.: WO2020/023312
PCT Pub. Date: Jan. 30, 2020

(65) Prior Publication Data
US 2021/0363241 A1  Nov. 25, 2021

Related U.S. Application Data

(60) Provisional application No. 62/795,744, filed on Jan. 23, 2019, provisional application No. 62/703,522, filed on Jul. 26, 2018.

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *A61K 2039/505* (2013.01); *C07K 2317/565* (2013.01); *C07K 2317/75* (2013.01); *C07K 2317/92* (2013.01)

(58) Field of Classification Search
None
See application file for complete search history.

(56) References Cited

U.S. PATENT DOCUMENTS 11,059,888 B2 * 7/2021 Shibuya ............. C07K 16/2803

FOREIGN PATENT DOCUMENTS

| CN | 102994449 A | 3/2013 |
| JP | 2013-193995 A | 9/2013 |
| WO | 2013140787 | 9/2013 |
| WO | 2018039332 | 3/2018 |
| WO | 2018102536 | 6/2018 |

OTHER PUBLICATIONS

Shibuya, et al., DNAM-1, a novel adhesion molecule involved in the cytolytic function of T lymphocytes. Immunity, 4:573-581, 1996.*
Stein et al., The paired receptors TIGIT and DNAM-1 as targets for therapeutic antibodies, Human Antibodies, 25(3-4):111-119, 2017.*
Okumura et al., Development and characterization of novel monoclaon antibodies aginast human DNAM-1, Monoclonal antibodies Immunodiagnosis Immunother. 36(3):135-139, Jun. 2017.*
Lamminmaki et al., Chrystal structure of a recombinant anti-estradiol Fab fragment in complex with the 17beta-estradiol, J. Biol. Chem. 276:36687-94, 2001.*
Carvalho et al., Rgulatory and scientific advancements in gene therapy: State-of-the-art of clinical applications and of the supporting European regulatory framework, Frontiers Med. 4:182, 18 pages, Oct. 2017.*
BD Pharmingen, Technical Data Sheet: Purified mouse anti-human CD266, Retrieved online: <URL: https://www.bdbiosciences.com/content/bdb/paths/generate-tds-document.us.559787.pdf> [retrieved on Apr. 27, 2022], 2017.*
International Search Report for PCT/US2019/042604.
Written Opinion for PCT/US2019/042604.
Zhang, et al., "DNAM-1 controls NK cell activation via an ITT-like motif," The Journal of Experimental Medicine, vol. 212, No. 12, pp. 2165-2182 (2015).
Stein, et al., "The paired receptors TIGIT and DNAM-1 as targets for therapeutic antibodies," Human Antibodies, vol. 25, No. 3-4, pp. 111-119 (2017).
Bottino, et al., "Identification of PVR (CD115) and Nectin-2 (CD112) as Cell Surface Ligands for the Human DNAM-1 (CD226) Activating Molecule," Journal of Experimental Medicine, vol. 198, No. 4, pp. 557-567 (2003).
Sloan, et al. "CD155/PVR plays a key role in cell motility during tumor cell invasion and migration," BMC Cancer, vol. 4, No. 73, pp. 1-14 (2004).
Blake, et al., "Molecular Pathways: Targeting CD96 and TIGIT for Cancer Immunotherapy," Clinical Cancer Research, vol. 22, No. 21, pp. 5183-5188 (2016).
Nakai, et al., "Overexpression of Necl-5 correlates with unfavorable prognosis in patients with lung adenocarcinoma," Cancer Science, vol. 101, No. 5, pp. 1326-1330 (2010).
Dardalhon, et al., "CD226 Is Specifically Expressed on the Surface of Th1 Cells and Regulates Their Expansion and Effector Functions," The Journal of Immunology, vol. 175, pp. 1558-1565 (2005).
Bottino, et al., "Natural killer cells and neuroblastoma: tumor recognition escape mechanisms, and possible novel immunotherapeutic approaches," Frontiers in Immunology, vol. 5, No. 56, 1-11 (2014).
Atsumi, et al., "Prognostic significance of CD155 nRNA expression in soft tissue sarcomas," Oncology Letters, vol. 5, pp. 1771-1776 (2013).
Vo, et al., "Expression of DNAM-1 (CD226) on inflammatory monocytes," Molecular Immunology, vol. 69, pp. 70-76 (2016).
Shengke Hou, et al., "CD226 Protein in Involved in Immune Synapse Formation and Triggers Natural Killer (NK) Cell Activation via Its First Extracellular Domain," The Journal of Biological Chemistry, vol. 289, No. 10, pp. 6969-6977 (2014).
Okumura, et al. "Development and Characterization of Novel Monoclonal Antibodies Against Human DNAM-1," Monoclonal Antibodies in Immunodiagnosis and Immunotherapy, vol. 36, No. 3, pp. 135-139 (2017).

(Continued)

*Primary Examiner* — Claire Kaufman
(74) *Attorney, Agent, or Firm* — Grant Reed

(57) ABSTRACT

The present invention relates to anti-human CD226 agonist antibodies, which can be useful for treating solid tumor cancers.

7 Claims, No Drawings
Specification includes a Sequence Listing.

(56) References Cited

OTHER PUBLICATIONS

Guillerey, et al., "Immunosurveillance and therapy of multiple myeloma are CD226 dependent," The Journal of Clinical Investigation, vol. 125, No. 5, pp. 2077-2089 (2015).
Isakov, "Immune Checkpoint-Targeted Therapy: Cancer and Autoimmune Diseases Represent Two Sides of the Same Coin," Journal of Autoimmune Disorders, vol. 2, No. 2:17, pp. 1-4 (2016).
Pauken, et al., "TIGIT and CD226: Tipping the Balance between Costimulatory and Coinhibitory Molecules to Augment the Cancer Immunotherapy Toolkit," Cancer Cell, vol. 26, pp. 785-787 (2014).
Hou, et al., "CD226 Protein is Involved in Immune Synapse Formation and Triggers Natural Killer (NK) Cell Activation via Its First Extracellular Domain," The Journal of Biological Chemistry, vol. 289, No. 10, pp. 6969-6977 (2014).
Tahara-Hanaoka, et al., "Tumor rejection by the poliovirus receptor family ligands of the DNAM-1 (CD226) receptor," Blood, vol. 107, No. 4, 1491-1496 (2006).
Carlsten, et al., "DNAX Accessory Molecule-1 Mediated Recognition of Freshly Isolated Ovarian Carcinoma by Resting Natural Killer Cells," Cancer Research, vol. 67, No. 3, pp. 1317-1324 (2007).
Nishiwada, et al., Clinical Significance of CD155 Expression in Human Pancreatic Cancer, vol. 35, No. 4, pp. 2287-2298 (2015).
Masson, et al., "Overexpression of the CD155 gene in human colorectal carcinoma," Gut, vol. 49, pp. 236-240 (2001).
Gaud, et al., "The costimulatory molecule CD226 signals through VAV1 to amplify TCR signals and promote IL-17 production by CD4+ T cells," Science Signaling, vol. 11, Issue 538, eaar 3083, pp. 1-13 (2018).
Gilfillan, et al., "DNAM-1 promotes activation of cytotoxic lymphocytes by nonprofessional antigen-presenting cells and tumors," The Journal of Experimental Medicine, vol. 205, No. 13, pp. 2965-2973 (2008).
Iguchi-Manaka, et al., "Accelerated tumor growth in mice deficient in DNAM-1 receptor," The Journal of Experimental Medicine, vol. 205, No. 13, pp. 2959-2964 (2008).
Dougall, et al, "TIGIT and CD96: new checkpoint receptor targets for cancer immunotherapy," Immunological Reviews, vol. 276, pp. 112-120 (2017).
Website—proteinatlas.org/ENSG00000150637-CD226/pathology, accessed Oct. 2, 2019.
Website—proteinatlas.org/ENSG00000130202-NECTIN2/pathology, accessed Oct. 2, 2019.
Website—proteinatlas.org/ENSG00000073008-PVR/pathology, accessed Oct. 2, 2019.
Tahara-Hanaoka, Satoko et al., Functional characterization of DNAM-1 (CD226) interaction with its ligands PVR (CD155) and nectin-2 (PRR-2/CD112), *International Immunology* 2004, (16(4): 533-538, The Japanese Society for Immunology.
English language abstract for CN 102994449 (2022).
English language abstract for JP Appl. No. 1012-63595, published as 2013-193995 (2022).

* cited by examiner

SEQUENCE LISTING

<160> NUMBER OF SEQ ID NOS: 14

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Ala Ala Ser Gly Phe Thr Phe Ser Ser Tyr Ala Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Ala Arg Asp Arg Trp Glu Leu His Asp Ala Phe Asp Ile
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Arg Ala Ser Gln Ser Ile Ser Ser Tyr Leu Asn
1               5                   10

```
<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Tyr Arg Ala Ser Thr Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Ser Tyr Ser Thr Pro Asp Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Glu Leu His Asp Ala Phe Asp Ile Trp Gly Gln
            100                 105                 110

Gly Thr Met Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Synthetic Construct

<400> SEQUENCE: 8

Val Ile Trp Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Arg Leu Leu Ile
        35                  40                  45
```

```
Tyr Arg Ala Ser Thr Leu Gln Ser Gly Val Pro Ser Arg Phe Ser Gly
         50                  55                  60

Asp Gly Ser Gly Thr His Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Asp
                 85                  90                  95

Thr Phe Gly Gln Gly Thr Lys Val Glu Ile Lys
                100                 105
```

<210> SEQ ID NO 9
<211> LENGTH: 450
<212> TYPE: PRT
<213> ORGANISM: Artificial Sequence
<220> FEATURE:
<223> OTHER INFORMATION: Synthetic Construct

<400> SEQUENCE: 9

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Trp Glu Leu His Asp Ala Phe Asp Ile Trp Gly Gln
                100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: Synthetic Structure

<400> SEQUENCE: 10

Val Ile Trp Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Arg Leu Leu Ile
        35                  40                  45

Tyr Arg Ala Ser Thr Leu Gln Ser Gly Val Pro Ser Arg Phe Ser Gly
50                  55                  60

Asp Gly Ser Gly Thr His Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 11
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 11

| gaggtgcagc | tgttggagtc | tgggggaggc | ttggtacagc | ctggggggtc | cctgagactc | 60 |
| tcctgtgcag | cctctggatt | cacctttagc | agctatgcca | tgagctgggt | ccgccaggct | 120 |
| ccagggaagg | ggctggagtg | ggtctcagct | attagtggta | gtggtggtag | cacatactac | 180 |
| gcagactccg | tgaagggccg | gttcaccatc | tccagagaca | attccaagaa | cacgctgtat | 240 |
| ctgcaaatga | acagcctgag | agccgaggac | acggccgtat | attactgtgc | gagagatcgg | 300 |
| tgggagcttc | atgatgcttt | tgatatctgg | ggccaaggga | caatggtcac | cgtctcttca | 360 |
| gctagcacca | agggcccatc | ggtcttcccc | ctggcaccct | cctccaagag | cacctctggg | 420 |
| ggcacagcgg | ccctgggctg | cctggtcaag | gactacttcc | ccgaaccggt | gacggtgtcg | 480 |
| tggaactcag | gcgcactgac | cagcggcgtg | cacaccttcc | cggctgtcct | acagtcctca | 540 |
| ggactctact | ccctcagcag | cgtggtgacc | gtgccctcca | gcagcttggg | cacccagacc | 600 |
| tacatctgca | acgtgaatca | caagcccagc | aacaccaagg | tggacaagag | agttgagccc | 660 |
| aaatcttgtg | acaaaactca | cacatgccca | ccgtgcccag | cacctgaagc | cgaggggggca | 720 |
| ccgtcagtct | tcctcttccc | cccaaaaccc | aaggacaccc | tcatgatctc | ccggacccct | 780 |
| gaggtcacat | gcgtggtggt | ggacgtgagc | cacgaagacc | ctgaggtcaa | gttcaactgg | 840 |
| tatgtggacg | gcgtggaggt | gcataatgcc | aagacaaagc | cgcggggagga | gcagtacaac | 900 |
| agcacgtacc | gtgtggtcag | cgtcctcacc | gtcctgcacc | aagactggct | gaatggcaag | 960 |
| gagtacaagt | gcaaggtctc | caacaaagcc | ctcccatcct | ccatcgagaa | aaccatctcc | 1020 |
| aaagccaaag | ggcagccccg | agaaccacag | gtgtacaccc | tgcccccatc | ccgggaggag | 1080 |
| atgaccaaga | accaagtcag | cctgacctgc | ctggtcaaag | gcttctatcc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctat | tccaagctca | ccgtggacaa | gagcaggtgg | 1260 |
| cagcagggga | acgtcttctc | atgctccgtg | atgcatgagg | ctctgcacaa | ccactacacg | 1320 |
| cagaagagcc | tctccctgtc | tccgggcaaa | | | | 1350 |

<210> SEQ ID NO 12
<211> LENGTH: 642
<212> TYPE: DNA
<213> ORGANISM: Artificial Sequence
<220> FEATURE:
<223> OTHER INFORMATION: Synthetic Construct

<400> SEQUENCE: 12

| gtcatctgga | tgacccagtc | tccatcctcc | ctgtctgcat | ctgtaggaga | cagagtcacc | 60 |
| atcacttgcc | gggcaagtca | gagcattagc | agctatttaa | attggtatca | gcagaaacca | 120 |
| gggaaagccc | ctaggctcct | gatctaccgt | gcatccactt | tacaaagtgg | ggtcccatca | 180 |
| aggttcagtg | gcgatggatc | tggaacacat | ttcactctca | ccatcagcag | cctccagcct | 240 |
| gaagattttg | caacttacta | ctgtcaacag | agttacagta | cccccgacac | ttttggccag | 300 |

```
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 13
<211> LENGTH: 336
<212> TYPE: PRT
<213> ORGANISM: Homo sapiens

<400> SEQUENCE: 13

```
Met Asp Tyr Pro Thr Leu Leu Ala Leu Leu His Val Tyr Arg Ala
1               5                   10                  15

Leu Cys Glu Glu Val Leu Trp His Thr Ser Val Pro Phe Ala Glu Asn
            20                  25                  30

Met Ser Leu Glu Cys Val Tyr Pro Ser Met Gly Ile Leu Thr Gln Val
        35                  40                  45

Glu Trp Phe Lys Ile Gly Thr Gln Gln Asp Ser Ile Ala Ile Phe Ser
    50                  55                  60

Pro Thr His Gly Met Val Ile Arg Lys Pro Tyr Ala Glu Arg Val Tyr
65                  70                  75                  80

Phe Leu Asn Ser Thr Met Ala Ser Asn Asn Met Thr Leu Phe Phe Arg
                85                  90                  95

Asn Ala Ser Glu Asp Asp Val Gly Tyr Tyr Ser Cys Ser Leu Tyr Thr
            100                 105                 110

Tyr Pro Gln Gly Thr Trp Gln Lys Val Ile Gln Val Val Gln Ser Asp
        115                 120                 125

Ser Phe Glu Ala Ala Val Pro Ser Asn Ser His Ile Val Ser Glu Pro
    130                 135                 140

Gly Lys Asn Val Thr Leu Thr Cys Gln Pro Gln Met Thr Trp Pro Val
145                 150                 155                 160

Gln Ala Val Arg Trp Glu Lys Ile Gln Pro Arg Gln Ile Asp Leu Leu
                165                 170                 175

Thr Tyr Cys Asn Leu Val His Gly Arg Asn Phe Thr Ser Lys Phe Pro
            180                 185                 190

Arg Gln Ile Val Ser Asn Cys Ser His Gly Arg Trp Ser Val Ile Val
        195                 200                 205

Ile Pro Asp Val Thr Val Ser Asp Ser Gly Leu Tyr Arg Cys Tyr Leu
    210                 215                 220

Gln Ala Ser Ala Gly Glu Asn Glu Thr Phe Val Met Arg Leu Thr Val
225                 230                 235                 240

Ala Glu Gly Lys Thr Asp Asn Gln Tyr Thr Leu Phe Val Ala Gly Gly
                245                 250                 255

Thr Val Leu Leu Leu Leu Phe Val Ile Ser Ile Thr Thr Ile Ile Val
            260                 265                 270

Ile Phe Leu Asn Arg Arg Arg Arg Glu Arg Asp Leu Phe Thr
        275                 280                 285

Glu Ser Trp Asp Thr Gln Lys Ala Pro Asn Asn Tyr Arg Ser Pro Ile
    290                 295                 300

Ser Thr Ser Gln Pro Thr Asn Gln Ser Met Asp Asp Thr Arg Glu Asp
305                 310                 315                 320
```

Ile Tyr Val Asn Tyr Pro Thr Phe Ser Arg Arg Pro Lys Thr Arg Val
              325                 330                 335

<210> SEQ ID NO 14
<211> LENGTH: 467
<212> TYPE: PRT
<213> ORGANISM: Artificial Sequence
<220> FEATURE:
<223> OTHER INFORMATION: Synthetic construct

<400> SEQUENCE: 14

Glu Glu Val Leu Trp His Thr Ser Val Pro Phe Ala Glu Asn Met Ser
1               5                   10                  15

Leu Glu Cys Val Tyr Pro Ser Met Gly Ile Leu Thr Gln Val Glu Trp
            20                  25                  30

Phe Lys Ile Gly Thr Gln Gln Asp Ser Ile Ala Ile Phe Ser Pro Thr
        35                  40                  45

His Gly Met Val Ile Arg Lys Pro Tyr Ala Glu Arg Val Tyr Phe Leu
    50                  55                  60

Asn Ser Thr Met Ala Ser Asn Asn Met Thr Leu Phe Phe Arg Asn Ala
65                  70                  75                  80

Ser Glu Asp Asp Val Gly Tyr Tyr Ser Cys Ser Leu Tyr Thr Tyr Pro
                85                  90                  95

Gln Gly Thr Trp Gln Lys Val Ile Gln Val Val Gln Ser Asp Ser Phe
            100                 105                 110

Glu Ala Ala Val Pro Ser Asn Ser His Ile Val Ser Glu Pro Gly Lys
        115                 120                 125

Asn Val Thr Leu Thr Cys Gln Pro Gln Met Thr Trp Pro Val Gln Ala
130                 135                 140

Val Arg Trp Glu Lys Ile Gln Pro Arg Gln Ile Asp Leu Leu Thr Tyr
145                 150                 155                 160

Cys Asn Leu Val His Gly Arg Asn Phe Thr Ser Lys Phe Pro Arg Gln
                165                 170                 175

Ile Val Ser Asn Cys Ser His Gly Arg Trp Ser Val Ile Val Ile Pro
            180                 185                 190

Asp Val Thr Val Ser Asp Ser Gly Leu Tyr Arg Cys Tyr Leu Gln Ala
        195                 200                 205

Ser Ala Gly Glu Asn Glu Thr Phe Val Met Arg Leu Thr Val Ala Glu
    210                 215                 220

Gly Lys Thr Asp Asn His Ile Glu Gly Arg Met Asp Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

-continued

```
Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

CD226 AGONIST ANTIBODIES

The present invention is in the field of medicine. More particularly, the present invention relates to agonist antibodies directed to human CD226 (hCD226), compositions comprising such agonist anti-human CD226 antibodies, and methods of using such agonist anti-human CD226 antibodies for the treatment of cancer.

Immune checkpoint pathways are involved in the suppression or activation of immune response (Isakov N, *J. Autoimmune Disorders* 2016; 2(2): 17). In autoimmune disease therapy, promoting, i.e., agonizing, the effect of an immune-suppressive pathway, such that the immune response is suppressed, can be desirable. Conversely, in cancer therapy, promoting, i.e., agonizing, the effect of an immune-stimulatory pathway, such that the immune response is activated, or stimulated, can be desirable.

CD226 functions as an immune co-stimulatory receptor (Dougall W C, et al., *Immunol. Rev.* 2017; 276: 112-120 (2017)). Thus, the CD226 pathway is an immune-stimulative pathway, i.e., it activates/stimulates the immune response (Manaka, I, A, *J. Exp. Med.;* 2008; 205(13): 2959-2964; Van Vo, A, *Molecular Immunology;* 2016; 69: 70-76; Shengke, H, *J Biol Chem.;* 2014; 289(10): 6969-6977). Promotion (agonism) of the immune-stimulative effect of the CD226 pathway may be beneficial, for example, in treating cancer, and a therapeutic molecule that promotes the immune-stimulative effect of the CD226 pathway is a CD226 pathway agonist.

CD226 is expressed on the surface of Natural killer (NK) cells, platelets, monocytes, CD8+ T cells and activated CD4+ T cells (Van Vo, A, *Molecular Immunology;* 2016; 69: 70-76), and in thyroid cancer, lung cancer, stomach cancer, colorectal cancer, head and neck cancer, urothelial cancer, prostate cancer, ovarian cancer, endometrial cancer, cervical cancer and melanoma (Protein Atlas, proteinatlas.org/ENSG00000150637-CD226/pathology).

CD226 interacts with CD112 (PVRL2) and CD155 (PVR), which are broadly expressed on hematopoietic, epithelial, and endothelial cells in many tissues in humans and mice (Van Vo, A, *Molecular Immunology;* 2016; 69: 70-76; Shengke, H, *The J of Biol. Chem.,* 2014; 289(10): 6969-6977). CD112 (PVLR2) is expressed in breast cancer, cervical cancer, colorectal cancer, endometrial cancer, head and neck cancer, liver cancer, lung cancer, melanoma, ovarian cancer, pancreatic cancer, prostate cancer, renal cancer, stomach (gastric) cancer, testicular cancer, thyroid cancer and urothelial cancer. (Human Protein Atlas proteinatlas.org/ENSG00000130202-NECTIN2/pathology).

CD155 (PVR) is expressed in lung cancer, liver cancer, pancreatic cancer, carcinoid, colorectal cancer, head and neck cancer, stomach cancer, renal cancer, urothelial cancer, testis cancer, prostate cancer, skin cancer and melanoma. (Human Protein Atlas, proteinatlas.org/ENSG00000073008-PVR/pathology). CD155 is also expressed in soft tissue sarcoma (Atsumi S, et al., Oncol. Lett. 2013; 5: 1771-1776).

Interactions between CD226 on NK cells and T cells, and CD112 and CD155 on tumor cells, and antigen presenting cells augment cell-mediated cytotoxicity and cytokine production (Iguchi-Manaka, A, *J. Exp. Med.* 2008; 205(13): 2959-2964 and references herein). CD226 is part of the CD226/TIGIT pathway, in which CD226 operates as an immune-stimulatory receptor, and TIGIT operates as an immune-suppressive receptor, and CD226 competes with TIGIT for binding to CD155 and CD112 (Dougall W C, et al., *Immunol. Rev.* 2017; 276: 112-120 (2017); *Blake, S, Clin Cancer Res;* 2016; 22(21): 5182-5188). TIGIT also inhibits CD226 homodimerization, which is necessary for CD226/CD155 interaction (Dougall W C, et al., *Immunol. Rev.* 2017; 276: 112-120 (2017)).

It has been suggested that agonizing the immune-stimulatory effect of CD226 may be beneficial in treating cancer (Pauken, K E and E J Wherry, *Cancer Cell* 2014: 26: 785-787). Thus, augmenting the anti-tumor immune response can be an effective means of cancer therapy. CD226 may be useful in controlling NK cell and T cell function, and it has been implicated in adhesion coreceptor stimulation of NK cell and CD8+ T cell-mediated cytotoxicity against tumor cells, immunological synapse formation, T cell proliferation and differentiation, and cytokine secretion. (Guillerey, C, *J. Clin. Invest.* 2015; 125(5): 2077-2089).

In mice lacking CD226, it was shown that CD8+ T cells required CD226 for co-stimulation when recognizing antigen presented by nonprofessional antigen-presenting cells, and NK cells required CD226 for the elimination of tumor cells that are comparatively resistant to NK cell-mediated cytotoxicity caused by the paucity of other NK cell-activating ligands S, *J. Exp. Med.;* 2008; 205(13): 2965-2973). CD226 thus extends the range of target cells that can activate CD8+ T cell and NK cells and, hence, may be important for immunosurveillance against tumors and/or viruses that evade recognition by other activating or accessory molecules (Gilfillan, S, *J. Exp. Med.;* 2008; 205(13): 2965-2973).

Certain anti-CD226 antibodies have been reported, such as mouse IgG1 KRA236 (Bottino, C, *Front Immunol.* 2014; 5: 56), rat IgG2a TX25 (Van Vo, A, *Molecular Immunology;* 2016; 69: 70-76); Rat IgG2b 10e5 (Dardalhon, V. *J Immunol* 2005; 175:1558-1565); mouse TX94, TX95, TX96, TX107, and TX108 (Okumura, G, *Monoclonal Antibodies in Immunodiagnosis and Immunotherapy,* 2017; 36(3): 135-139), 2E6 and 3B9 (Hou, S, *The J. Biol.* Chemistry; 2014; 289(10): 6969-6977), NewE1 (Gaud, G, et al., *Sci. Signal.* 2018; 11: eaar3083; doi: 10.1126/scisignal.aar3083), DX11 (Bio-Rad MCA2257), 11A8 (BioLegend 338311), and LeoA1 (Millipore Sigma MABT398).

However, no human anti-human CD226 agonist antibodies have been reported, and there are no anti-CD226 antibodies in clinical development for the treatment of cancer. Thus, there exists a need for agonist antibodies that bind to the human CD226, enhance the immune response, and are useful in treatment of cancer.

The anti-human CD226 agonist antibodies described herein bind to human CD226, stimulate T cell derived IFNγ production, and inhibit tumor growth in a murine tumor model as a monotherapy. In one embodiment, an antibody of the present invention demonstrates desired physical and chemical stability including, but not limited to, in vivo stability, thermal stability, solubility, low self-association, and pharmacokinetic characteristics and, therefore, are potentially useful in treating cancer. In another embodiment, an anti-human CD226 agonist antibody of the present invention is a fully human antibody. In another embodiment, an anti-human CD226 agonist antibody of the present invention is a humanized antibody.

The present disclosure also provides a human anti-human CD226 IgG1-effector null (IgG1-EN) antibody that binds human CD226 (SEQ ID NO: 13), or an extracellular fragment thereof (for example, SEQ ID NO: 14), and inhibits tumor growth in murine tumor models of cancer as a monotherapy, the anti-human CD226 antibody comprising an HCDR1 having the amino acid sequence of SEQ ID NO:

1, an HCDR2 having the amino acid sequence of SEQ ID NO: 2, an HCDR3 having the amino acid sequence of SEQ ID NO: 3, an LCDR1 having the amino acid sequence of SEQ ID NO: 4, an LCDR2 having the amino acid sequence of SEQ ID NO: 5, and an LCDR3 having the amino acid sequence of SEQ ID NO: 6. In another embodiment, the present disclosure provides that the antibody comprises a heavy chain variable region (HCVR) having the amino acid sequence of SEQ ID NO: 7 and a light chain variable region (LCVR) having the amino acid sequence of SEQ ID NO: 8. In another embodiment, the present disclosure provides that the antibody comprises a heavy chain (HC) having the amino acid sequence of SEQ ID NO: 9, and a light chain (LC) having the amino acid sequence of SEQ ID NO: 10. In another embodiment, the present disclosure provides that the antibody consists of two heavy chains having the amino acid sequence of SEQ ID NO: 9, and two light chains having the amino acid sequence of SEQ ID NO: 10.

The present disclosure also provides a mammalian cell capable of expressing an anti-human CD226 antibody comprising: an HCDR1 having the amino acid sequence of SEQ ID NO: 1, an HCDR2 having the amino acid sequence of SEQ ID NO: 2, an HCDR3 having the amino acid sequence of SEQ ID NO: 3, an LCDR1 having the amino acid sequence of SEQ ID NO: 4, an LCDR2 having the amino acid sequence of SEQ ID NO: 5, and an LCDR3 having the amino acid sequence of SEQ ID NO: 6. In another embodiment, the present disclosure provides that the anti-human CD226 antibody comprises an HCVR having the amino acid sequence of SEQ ID NO: 7 and an LCVR having the amino acid sequence of SEQ ID NO: 8. In another embodiment, the present disclosure provides that the antibody comprises a HC having the amino acid sequence of SEQ ID NO: 9, and a LC having the amino acid sequence of SEQ ID NO: 10. In another embodiment, the present disclosure provides that the antibody consists of two heavy chains having the amino acid sequence of SEQ ID NO: 9, and two light chains having the amino acid sequence of SEQ ID NO: 10.

The present disclosure also provides a process for producing an anti-human CD226 antibody, comprising cultivating a mammalian cell capable of expressing the antibody and recovering the antibody, wherein the antibody comprises an HCDR1 having the amino acid sequence of SEQ ID NO: 1, an HCDR2 having the amino acid sequence of SEQ ID NO: 2, an HCDR3 having the amino acid sequence of SEQ ID NO: 3, an LCDR1 having the amino acid sequence of SEQ ID NO: 4, an LCDR2 having the amino acid sequence of SEQ ID NO: 5, and an LCDR3 having the amino acid sequence of SEQ ID NO: 6. In another embodiment, the present disclosure provides that the antibody comprises an HCVR having the amino acid sequence of SEQ ID NO: 7 and an LCVR having the amino acid sequence of SEQ ID NO: 8. In another embodiment, the present disclosure provides that the antibody comprises a HC having the amino acid sequence of SEQ ID NO: 9, and a LC having the amino acid sequence of SEQ ID NO: 10. In another embodiment, the present disclosure provides that the antibody consists of two heavy chains having the amino acid sequence of SEQ ID NO: 9, and two light chains having the amino acid sequence of SEQ ID NO: 10. The present disclosure also provides the anti-human CD226 antibody produced by the process. The present disclosure also provides a pharmaceutical composition comprising the anti-human CD226 antibody produced by the process and an acceptable carrier, diluent, or excipient.

The present disclosure also provides a DNA molecule comprising a polynucleotide having the sequence of SEQ ID NO: 11, SEQ ID NO: 12, or SEQ ID NOS: 11 and 12. The present disclosure also provides a mammalian cell comprising a DNA molecule comprising a polynucleotide having the sequence of SEQ ID NO: 11, SEQ ID NO: 12, or SEQ ID NOS: 11 and 12.

The present disclosure also provides a pharmaceutical composition comprising an anti-human CD226 antibody comprising: an HCDR1 having the amino acid sequence of SEQ ID NO: 1, an HCDR2 having the amino acid sequence of SEQ ID NO: 2, an HCDR3 having the amino acid sequence of SEQ ID NO: 3, an LCDR1 having the amino acid sequence of SEQ ID NO: 4, an LCDR2 having the amino acid sequence of SEQ ID NO: 5, and an LCDR3 having the amino acid sequence of SEQ ID NO: 6, and an acceptable carrier, diluent, or excipient. In another embodiment, the present disclosure provides that the anti-human CD226 antibody comprising an HCVR having the amino acid sequence of SEQ ID NO: 7 and an LCVR having the amino acid sequence of SEQ ID NO: 8. In some embodiments, the anti-human CD226 antibody comprises an HC having the amino acid sequence of SEQ ID NO: 9, and an LC having the amino acid sequence of SEQ ID NO: 10. In some embodiments, the anti-human CD226 antibody consists of two heavy chains having the amino acid sequence of SEQ ID NO: 9, and two light chains having the amino acid sequence of SEQ ID NO: 10.

The present disclosure provides methods of treatment and methods for use. The role of the CD226 as a co-stimulatory receptor in the immune system has been studied. For example, mice deficient for CD226, showed significantly less cytotoxic activity against CD226 ligand-expressing tumors in vitro than wild-type (WT) cells (Iguchi-Manaka, A, *J. Exp. Med.* 2008; 205(13): 2959-2964). Thus, when the CD226 pathway is activated, immune system activity increases, which can be exploited in treating cancer by stimulating (agonizing) the CD226 pathway, and an agonist anti-human CD226 antibody may provide a therapeutic effect against cancer by activating NK cell and/or T cell activity.

CD112 and/or CD155 expression has been implicated in a variety of human solid including colorectal carcinoma (Masson, D., Gut, 2001; 49: 236-240; Tahara-Hanaoka, S. *Blood,* 2006; 107: 1491-1496); gastric cancer (Tahara-Hanaoka, S., *Blood,* 2006; 107: 1491-1496); ovarian cancer (Carlsten, M., *Cancer Res.,* 2007: 67: 1317-1325); pancreatic carcinoma (Nishiwada, *Anticancer Research;* 2015; 35: 2287-2298); and in prostate, renal cell, pancreatic, colon, non-small cell lung, ovarian, and breast carcinomas (Sloan, K., *BMC Cancer* 2004; 4: 73).

Over-expression of CD155 in lung adenocarcinomas, was significantly associated with lymph node metastasis, bronchioloalveolar carcinoma ratio of tumors and the disease-free survival rate in patients with positive CD155 overexpression was significantly lower than that in patients with negative CD155 overexpression (Nakai, R, *Cancer Sci.;* 2010; 101(5): 1326-1330). Multivariate survival analysis revealed CD155 expression to be an independent risk factor for an unfavorable outcome (Nakai, R, *Cancer Sci.;* 2010; 101(5): 1326-1330).

The present disclosure provides a method of treating cancer, comprising administering to a patient in need thereof an effective amount of an anti-human CD226 antibody, comprising an HCDR1 having the amino acid sequence of SEQ ID NO: 1, an HCDR2 having the amino acid sequence of SEQ ID NO: 2, an HCDR3 having the amino acid sequence of SEQ ID NO: 3, an LCDR1 having the amino acid sequence of SEQ ID NO: 4, an LCDR2 having the amino acid sequence of SEQ ID NO: 5, and an LCDR3 having the amino acid sequence of SEQ ID NO: 6. In another embodiment, the present disclosure also provides that the antibody comprises an HCVR having the amino acid sequence of SEQ ID NO: 7 and an LCVR having the amino acid sequence of SEQ ID NO: 8. In another embodiment, the present disclosure also provides that the antibody comprises an HC having the amino acid sequence of SEQ ID NO: 9 and an LC having the amino acid sequence of SEQ ID NO: 10. In another embodiment, the present disclosure also provides that the antibody consists of two heavy chain having the amino acid sequence of SEQ ID NO: 9 and two light chains having the amino acid sequence of SEQ ID NO: 10.

In some embodiments, the present disclosure also provides that the cancer is a solid tumor cancer. In another embodiment, the present disclosure also provides that the solid tumor cancer is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, soft tissue sarcoma, stomach (gastric) cancer, testicular cancer, thyroid cancer, uterine cancer or urothelial cancer. In a preferred embodiment, the lung cancer is non-small cell lung cancer. In another preferred embodiment, the breast cancer is triple-negative breast cancer.

The present disclosure provides an anti-human CD226 antibody that binds to human CD226 (SEQ ID NO: 13), or to an extracellular fragment thereof (for example, SEQ ID NO: 14), comprising an HCDR1 having the amino acid sequence of SEQ ID NO: 1, an HCDR2 having the amino acid sequence of SEQ ID NO: 2, an HCDR3 having the amino acid sequence of SEQ ID NO: 3, an LCDR1 having the amino acid sequence of SEQ ID NO: 4, an LCDR2 having the amino acid sequence of SEQ ID NO: 5, and an LCDR3 having the amino acid sequence of SEQ ID NO: 6, for use in therapy. In another embodiment, the present disclosure provides that the antibody comprises an HCVR having the amino acid sequence of SEQ ID NO: 7 and an LCVR having the amino acid sequence of SEQ ID NO: 8. In another embodiment, the present disclosure provides that the antibody comprises an HC having the amino acid sequence of SEQ ID NO: 9, and an LC having the amino acid sequence of SEQ ID NO: 10. In another embodiment, the present disclosure provides that the antibody consists of two heavy chains having the amino acid sequence of SEQ ID NO: 9, and two light chains having the amino acid sequence of SEQ ID NO: 10.

In one embodiment, the present disclosure provides that the therapy is the treatment of cancer. In another embodiment, the present disclosure provides that the cancer is a solid tumor cancer. In another embodiment, the present disclosure provides that the solid tumor cancer is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, soft tissue sarcoma, stomach (gastric) cancer, testicular cancer, thyroid cancer, uterine cancer or urothelial cancer. In a preferred embodiment, the lung cancer is non-small cell lung cancer. In another preferred embodiment, the breast cancer is triple-negative breast cancer.

The present disclosure also provides the use of an anti-human CD226 antibody that binds to human CD226 (SEQ ID NO: 13), or to an extracellular fragment thereof (for example, SEQ ID NO: 14), comprising an HCDR1 having the amino acid sequence of SEQ ID NO: 1, an HCDR2 having the amino acid sequence of SEQ ID NO: 2, an HCDR3 having the amino acid sequence of SEQ ID NO: 3, an LCDR1 having the amino acid sequence of SEQ ID NO: 4, an LCDR2 having the amino acid sequence of SEQ ID NO: 5, and an LCDR3 having the amino acid sequence of SEQ ID NO: 6, for the manufacture of a medicament for the treatment of cancer. In another embodiment, the present disclosure provides that the antibody comprises an HCVR having the amino acid sequence of SEQ ID NO: 7 and an LCVR having the amino acid sequence of SEQ ID NO: 8. In another embodiment, the present disclosure provides that the antibody comprises an HC having the amino acid sequence of SEQ ID NO: 9 and an LC having the amino acid sequence of SEQ ID NO: 10. In another embodiment, the present disclosure provides that the antibody consists of two heavy chains having the amino acid sequence of SEQ ID NO: 9 and two light chains having the amino acid sequence of SEQ ID NO: 10.

In one embodiment, the present disclosure also provides that the cancer is a solid tumor cancer. In another embodiment, the present disclosure also provides that the solid tumor cancer is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, stomach (gastric) cancer, testicular cancer, thyroid cancer, uterine cancer or urothelial cancer. In a preferred embodiment, the lung cancer is non-small cell lung cancer. In another preferred embodiment, the breast cancer is triple-negative breast cancer.

The present disclosure also provides a human anti-human CD226 agonist antibody. In one embodiment, the human anti-human antibody has an an anti-tumoreffect when administered in vivo. The present disclosure provides a mammalian cell capable of expressing the human anti-human antibody. The present disclosure also provides a process for producing a human anti-human CD226 antibody, comprising: cultivating a mammalian cell capable of expressing the antibody, and recovering the antibody.

The present disclosure also provides a human anti-human CD226 antibody for use in therapy. In one embodiment, the human anti-human CD226 antibody is an agonist antibody. In another embodiment, the human anti-human CD226 antibody stimulates an immune response. In another embodiment, the human anti-human CD226 antibody has an anti-tumor activity when administered in vivo.

The present disclosure also provides a human anti-human CD226 antibody, for use in the treatment of cancer. In one embodiment, the present disclosure provides a human anti-human CD226 agonist antibody for use in the treatment of a solid tumor cancer. In another embodiment, the antibody stimulates an immune response. In another embodiment, the antibody has an anti-tumor activity when administered in vivo.

In one embodiment, the present disclosure provides the human anti-human CD226 antibody, for use in the treatment of a solid tumor cancer. In another embodiment, present disclosure provides that the solid tumor cancer is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, soft tissue sarcoma, stomach (gastric) cancer, testicular cancer, thyroid cancer, uterine cancer or urothelial cancer. In a preferred embodiment, the lung cancer is non-small cell lung cancer. In another preferred embodiment, the breast cancer is triple-negative breast cancer.

The present disclosure provides the use of a human anti-human CD226 agonist antibody for the manufacture of a medicament for the treatment of cancer. In one embodiment, the present disclosure provides that the cancer is a solid tumor cancer. In another embodiment, the present disclosure provides that the solid tumor cancer is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, soft tissue sarcoma, stomach (gastric) cancer, testicular cancer, thyroid cancer, uterine cancer or urothelial cancer. In a preferred embodiment, the lung cancer is non-small cell lung cancer. In another preferred embodiment, the breast cancer is triple-negative breast cancer.

In one embodiment, the present invention provides a method of treating cancer, comprising administering an effective amount of an antibody disclosed herein in simultaneous, separate, or sequential combination with one or more anti-tumor agents. Non-limiting examples of anti-tumor agents include ramucirumab, necitumumab, olaratumab, gemcitabine, pemetrexed, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), cetuximab, an EGFR inhibitor, a Raf inhibitor, a B-Raf inhibitor, a CDK4/6 inhibitor, a CDK7 inhibitor, an idoleamine 2,3-dioxygenase inhibitor, a TGFβ inhibitor, a TGFβ receptor inhibitor, IL-10, and pegylated IL-10 (e.g., pegilodecakin).

In a another embodiment, the present invention provides a method of treating cancer, comprising administering an effective amount of a compound of an antibody disclosed herein in simultaneous, separate, or sequential combination with one or more immuno-oncology agents. Non-limiting examples of immuno-oncology agents include nivolumab, ipilimumab, pidilizumab, pembrolizumab, tremelimumab, urelumab, lirilumab, atezolizumab, durvalumab, an anti-Tim3 antibody, an anti-PD-1 antibody, an anti-PD-L1 antibody, and the anti-PD-L1 antibody LY3300054 (the heavy and light chain sequences of which are forth in WO 2017/034916 and US 2017/0058033 as SEQ ID NOS: 10 and 11, respectively). In another preferred embodiment, the immune-oncology agent is an anti-PD-1 antibody. In another preferred embodiment, the anti-PD-1 antibody is pembrolizumab.

In another embodiment, the CD226 antibody comprises: an HCVR having the amino acid sequence of SEQ ID NO: 7 and an LCVR having the amino acid sequence of SEQ ID NO: 8. In another embodiment, the present invention provides a mammalian cell capable of expressing the antibody; a process for producing an antibody, comprising cultivating the mammalian cell, and recovering the antibody; an antibody produced by the process; and a pharmaceutical composition, comprising the antibody, and an acceptable carrier, diluent, or excipient.

In another embodiment, the CD226 antibody comprises: an HC having the amino acid sequence of SEQ ID NO: 9, and an LC having the amino acid sequence of SEQ ID NO: 10. In another embodiment, the present invention provides a mammalian cell capable of expressing the antibody; a process for producing an antibody, comprising cultivating the mammalian cell, and recovering the antibody; an antibody produced by the process; and a pharmaceutical composition, comprising the antibody, and an acceptable carrier, diluent, or excipient.

In another embodiment, the CD226 antibody consists of: two heavy chains having the amino acid sequence of SEQ ID NO: 9, and two light chains having the amino acid sequence of SEQ ID NO: 10. In another embodiment, the present disclosure also provides a mammalian cell capable of expressing the antibody; a process for producing an antibody, comprising cultivating the mammalian cell, and recovering the antibody; an antibody produced by the process; and a pharmaceutical composition, comprising the antibody, and an acceptable carrier, diluent, or excipient.

The present disclosure also provides a DNA molecule comprising a polynucleotide having: the sequence of SEQ ID NO: 11, SEQ ID NO: 12, or SEQ ID NOS: 11 and 12; a mammalian cell comprising the DNA molecule.

The present disclosure also provides a method of treating cancer, comprising administering to a patient in need thereof, an effective amount of an antibody of the present invention.

The present disclosure also provides the antibody of the present invention, for use in therapy. In one embodiment, the present disclosure also provides that the use is treating cancer.

The present disclosure also provides an antibody of the present invention for the manufacture of a medicament for the treatment of cancer.

In one embodiment, the present disclosure also provides that the cancer is a solid tumor cancer. In another embodiment, the solid tumor cancer is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, soft tissue sarcoma, (gastric) cancer, testicular cancer, thyroid cancer, uterine cancer or urothelial cancer. In a preferred embodiment, the lung cancer is non-small cell lung cancer. In another preferred embodiment, the breast cancer is triple-negative breast cancer.

In one preferred embodiment, the present invention provides an anti-human CD226 antibody that binds to human CD226 and blocks CD226 binding to CD112, but does not block binding to CD155.

In another preferred embodiment, the present invention also provides an anti-human CD226 antibody that exhibits agonist function, i.e., that stimulates T cell activity in CD226+ T cells exposed to the anti-human CD226 antibody in vitro, e.g., increased interferon-gamma secretion in vitro, relative to the level of interferon-gamma secretion in vitro by CD226+ T cells that are not exposed to the anti-human CD226 antibody. In one embodiment, interferon-gamma secretion can be assayed using a method disclosed herein.

In another preferred embodiment, the present invention also provides an anti-human CD226 antibody that exhibits agonist function, i.e., that induces NF-κB activation reporter gene in human embryonic kidney (HEK) cells, as disclosed herein, relative to HEK cells that are not exposed to the anti-human CD226 antibody in vitro, e.g., as disclosed herein.

In another preferred embodiment, the present invention provides an anti-human CD226 antibody that does not activate platelets. In one embodiment, the assay is performed using flow cytometry to determine the expression of p-selection (CD62P) on the platelet surface to determine the activation status of platelets.

The term "antibody" as used herein refers to a polypeptide complex having two heavy chains (HC) and two light chains (LC) such that the heavy chains and lights chains are interconnected by disulfide bonds; wherein the antibody is an IgG subclass antibody. Each HC is comprised of an N-terminal HCVR and a heavy chain constant region ("HCCR"). Each LC is comprised of an N-terminal LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

An antibody of the present invention is a non-naturally occurring polypeptide complex. A DNA molecule of the present invention is a DNA molecule that comprises a non-naturally occurring polynucleotide sequence encoding a polypeptide having the amino acid sequence of at least one of the polypeptides in an antibody of the present invention.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the HC are referred to as "HCDR1, HCDR2, and HCDR3" and the three CDRs of the LC are referred to as "LCDR1, LCDR2 and LCDR3". The CDRs contain most of the residues which form specific interactions with the antigen.

An isolated DNA encoding a HCVR region can be converted to a full-length HC gene by operably linking the HCVR-encoding DNA to another DNA molecule encoding HCCRs. The sequences of human, as well as other mammalian, HCCR genes are known in the art. DNA fragments encompassing these regions can be obtained e.g., by standard PCR amplification.

An isolated DNA encoding a LCVR region may be converted to a full-length LC gene by operably linking the LCVR-encoding DNA to another DNA molecule encoding a LC constant region. The sequences of human, as well as other mammalian, LCCR genes are known in the art. DNA fragments encompassing these regions can be obtained by standard PCR amplification. The LCCR can be a kappa or lambda constant region. Preferably for antibodies of the present invention, the LCCR is a kappa constant region.

The polynucleotides of the present invention can be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibodies of the present invention can readily be produced in mammalian cells, non-limiting examples of which include CHO, NS0, HEK 293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, N.Y. (1994).

In other embodiments of the present invention, the antibody (or the nucleic acids encoding the same) is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

An antibody of the present invention, or pharmaceutical compositions comprising the same, may be administered by parenteral routes, non-limiting examples of which are subcutaneous administration and intravenous administration. An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy,* $22^{nd}$ ed. (2012), A. Loyd et al., Pharmaceutical Press) and comprise an antibody, as disclosed herein, and one or more pharmaceutically acceptable carriers, diluents, or excipients.

As used herein, "CD226" refers to the receptor that has the amino acid sequence set forth in SEQ ID NO: 13; uniprot.org/uniprot/Q15762. An example of a CD226 extracellular domain-His tag construct is found at rndsystems-.com, Product No. Q154762.

Synonyms for "CD226" are DNAX accessory molecule-1, DNAM-1, DNAM1, PTA1 and TLiSA1.

As used herein, "anti-human CD226 agonist antibody" refers to an antibody that (a) binds to human CD226 (SEQ ID NO: 13), or to an extracellular fragment thereof (for example, SEQ ID NO: 14), (b) stimulates an immune response in vitro, e.g., as assayed in a T cell cytokine (e.g., IFN-gamma) release assay as disclosed herein, or in vivo, e.g., as assayed by T cell cytokine (e.g., IFN-gamma) release in the blood or serum of a subject, and (c) when administered in vivo to a subject, results in an anti-tumor activity.

In the context of monoclonal therapeutic antibodies, the terms "human," "humanized" and "fully human" are well known to those of ordinary skill in the art (Weiner L J, *J. Immunother.* 2006; 29: 1-9; Mallbris L, et al., *J. Clin. Aesthet. Dermatol.* 2016; 9: 13-15).

Synonyms for "CD155" are poliovirus receptor, PVR, Necl-5, NECL5, Tage4, HVED and PVS.

Synonyms for "CD112" are Nectin cell adhesion molecule 2, nectin-2, NECTIN2, PRR-2, PVRL2, PVRR2 and HVEB.

The immune-stimulatory effect of the CD226 pathway for example, can be mediated by association with LFA-1 on the cell surface which potentiates activating signals. LFA-1 engagement results in Fyn kinase-mediated phosphorylation of the CD226R cytoplasmic domain (Marcus, A, *Adv Immunol.* 2014; 122: 91-128). In another example, CD226 can also mediate active biochemical signals that are essential for its capacity to enhance NK cell cytotoxicity and cytokine production; these signals are initiated by a conserved ITT or ITT-like motif (pYxNx), which undergoes phosphorylation by Src family kinases and recruits the adaptor Grb2. In turn, Grb2 activates Vav-1, PI3′K, and PLC-yl, which leads to activation of Erk, Akt, and calcium fluxes. Such a pathway promotes actin polymerization and granule polarization, thereby enhancing cytotoxicity. As CD226 is expressed in other immune cells, including $CD8^+$ T cells, it is reasonable to speculate that CD226 mediates similar signals and effects in these cells. (Zhang, Z, *JEM*, 2015; 212(12): 2165).

Methods for assaying CD226 activity in vitro are known to those of ordinary skill in the art, for example in Gaud, G, et al., *Sci. Signal.* 2018; 11: eaar3083; doi: 10.1126/scisignal.aar3083.

In vivo murine models of solid tumor are well known to those of ordinary skill in the art, as shown herein, and as disclosed, e.g., in Sanmamed M F, et al., *Ann. Oncol.* 2016; 27: 1190-1198; Manning H C, et al., *J Nucl. Med* 2016; 57(Suppl. 1): 60S-68S; Teich B A. *Cancer Ther.* 2006; 5: 2435; Rongvaux A, et al., *Ann. Rev. Immunol.* 2013; 31: 635-74; Stylli SS, et al., *J Clin. Neurosci* 2015; 619-26; Oh T, et al., *J Transl. Med.* 2014; 12: 107-117; Newcomb, E W, et al., *Radiation Res.* 2010; 173: 426-432; Song Y, et al., *Proc Natl. Acad. Sci. USA* 2013; 110: 17933-8; and Rutter E M, et al., *Scientific Reports* 2017; 7: DOI:10.1038/s41598-017-02462-0.

As used herein, with respect to a solid tumor, the term "anti-cancer activity" refers to the shrinkage in size of a tumor; a decrease in the progression of cancer in a patient from one stage to another stage in patients treated with an anti-CD226 agonist antibody, relative to patients who are not treated with an anti-CD226 agonist antibody; or a decrease in the incidence of metastatic cancer in patients treated with an anti-CD226 agonist antibody, relative to patients who are not treated with an anti-CD226 agonist antibody.

In the context of clinical solid tumor cancer treatment, activation (agonism) of the immune-stimulatory effect of the CD226 pathway can be assessed by examining tumor regression using techniques well known to those of ordinary skill in the art, for example, using one or more of X-ray imaging, magnetic resonance imaging (MRI), positron-emission tomography, ultrasound imaging, tissue biopsy, tumor biopsy, surgical access and visual review, pathology analysis, immunohistochemistry, body fluid or tissue biomarker analysis, physical inspection and palpation.

Dosage regimens may be adjusted to provide the optimum desired response (e.g., a therapeutic effect). Treatment dosages may be titrated to optimize safety and efficacy. Dosing schedules, for intravenous (i.v.) or non-intravenous administration, localized or systemic, or combinations thereof, will typically range from a single bolus dosage or continuous infusion to multiple administrations per day (e.g., every 4-6 hours), or as indicated by the treating physician and the patient's condition. Dosing amounts and frequencies may be determined by the physicians treating the patient.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

An effective amount can be readily determined by one skilled in the art, by the use of known techniques, and by observing results obtained under analogous circumstances.

In determining the effective amount for a patient, a number of factors are considered by the attending diagnostician, including, but not limited to: the patient's size, age, and general health; the specific disease or disorder involved; the degree of, or involvement, or the severity of the disease or disorder; the response of the individual patient; the particular compound administered; the mode of administration; the bioavailability characteristics of the preparation administered; the dose regimen selected; the use of concomitant medication; and other relevant circumstances.

As used herein, the term "effective response" of a patient or a patient's "responsiveness" to treatment refers to the clinical or therapeutic benefit imparted to a patient upon administration an antibody of the present disclosure. Such benefit includes any one or more of: extending survival (including overall survival and progression free survival); resulting in an objective response (including a complete response or a partial response); stabilized disease; or improving signs or symptoms of cancer, etc.

A potential advantage of methods disclosed herein is the possibility of producing marked and/or prolonged anti-tumor activity in a patient with an acceptable safety profile including acceptable tolerability, toxicities and/or adverse events, so that the patient benefits from the treatment method overall. The efficacy of the treatment of the present disclosure can be measured by various endpoints commonly used in evaluating cancer treatments, including but not limited to, tumor regression, tumor weight or size shrinkage, time to progression, overall survival, progression free survival, overall response rate, duration of response, and quality of life.

As used herein, the term "solid tumor" refers to a tumor in a tissue that is not blood, lymphatics or bone marrow.

As used herein, the term "Complete Response (CR)" refers to the disappearance of all target lesions. Any pathological lymph nodes (whether target or non-target) must have reduction in short axis to <10 mm. Tumor marker results must have normalized.

As used herein, the term "Partial Response (PR)" means at least a 30% decrease in the sum of diameter of target lesions, taking as reference the baseline sum diameters.

As used herein the term "Progressive Disease (PD)" means at least a 20% increase in the sum of the diameters of target lesions, taking as reference the smallest sum on study (including the baseline sum if that is the smallest). In addition to the relative increase of 20%, the sum must also demonstrate an absolute increase of at least 5 mm. The appearance of 1 or more new lesions is also considered progression. For equivocal findings of progression (for example, very small and uncertain new lesions; cystic changes or necrosis in existing lesions), treatment may continue until the next scheduled assessment. If at the next scheduled assessment, progression is confirmed, the date of progression should be the earlier date when progression was suspected.

As used herein, the term "Progression-Free Survival (PFS)" is defined as the time from the date of first dose of any study drug until the date of radiographically documented PD or death due to any cause, whichever is earlier.

As used herein, the term "Overall Survival (OS)" is defined as the time from the date of study first dose of any study drug to the date of death from any cause.

As used herein "Antibody 1" refers to an antibody having the HCDR1 amino acid sequence of SEQ ID NO: 1, the HCDR2 amino acid sequence of SEQ ID NO: 2, the HCDR3 amino acid sequence of SEQ ID NO: 3, the LCDR1 amino acid sequence of SEQ ID NO: 4, the LCDR2 amino acid sequence of SEQ ID NO: 5, the LCDR3 amino acid sequence of SEQ ID NO: 6, the HCVR amino acid sequence of SEQ ID NO: 7, the LCVR amino acid sequence of SEQ ID NO: 8, the HC amino acid sequence of SEQ ID NO: 9, the LC amino acid sequence of SEQ ID NO: 10, the HC DNA sequence of SEQ ID NO: 11, and the LC DNA sequence of SEQ ID NO: 12.

The framework and CDR sequences in each of the antibodies for which sequences are set forth herein are annotated using annotation rules in agreement with the method of North, et al. *J. Mol. Biol.* 2011: 406: 228-256.

The sequence identifiers used herein are listed in Table 1.

TABLE 1

Sequence Identifiers Used Herein

| SEQ ID NO: (Amino Acid) | Antibody 1 |
| --- | --- |
| HCDR1 | 1 |
| HCDR2 | 2 |
| HCDR3 | 3 |
| LCDR1 | 4 |
| LCDR2 | 5 |
| LCDR3 | 6 |
| HCVR | 7 |
| LCVR | 8 |
| Heavy chain | 9 |
| Light chain | 10 |

| SEQ ID: (DNA) | Antibody 1 |
| --- | --- |
| HC | 11 |
| LC | 12 |

Human CD226 (Amino Acid): SEQ ID NO: 13
Human CD226-ECD-Fc (Amino Acid): SEQ ID NO: 14

Antibody Characterization, Generation, Expression, and Purification

Antibody production using the HC polynucleotide sequence shown in SEQ ID NO: 11, and the LC polynucleotide sequence shown in SEQ ID NO: 12 in mammalian cells results in the production of a full length antibody (hereafter referred to as "Antibody 1") having the HC amino acid sequence shown in SEQ ID NO: 9 and the LC amino acid sequence of SEQ ID NO: 10.

The antibodies of the present invention may be generated by using known methods, including but not limited to, phage display. Additionally, the antibodies derived as described above may be further screened using the assays described herein.

The polypeptides of the variable regions of the HC and LC and the complete HC and LC amino acid sequences of Antibody 1, and the nucleotide sequences encoding the same, are listed in the section entitled "Amino Acid and Nucleotide Sequences."

The sequence for human CD226 is set forth in SEQ ID NO: 13, and the sequence for a human CD226 extracellular domain (ECD)-Fc fusion is set forth in SEQ ID NO: 14.

The antibodies of the present invention, including, but not limited to, Antibody 1 can be made and purified, for example, essentially as follows. An appropriate host cell, for example, HEK 293 or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KapnaSelect column (GE Healthcare), that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by UV absorbance or SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The product may be immediately frozen at −70° C. or may be lyophilized.

Antibody 1 Binds to Human CD226

The ability of the antibodies disclosed herein to bind human CD226 can be measured by ELISA. To measure binding to human CD226, a 96-well plate (Immulon 2HB) is coated with human CD226-Fc (R&D Systems) overnight at 4° C. Wells are blocked for 2 h with blocking buffer (PBS containing 1% bovine serum albumin). Wells are washed three times with PBS containing 0.1% Tween-20. Antibody 1 or control IgG (100 µL) is then added at different concentrations and incubated at room temperature for 1 h. After washing, the plate is incubated with 100 µL of goat anti-human IgG F(ab')2-HRP conjugate (Jackson Immuno Research Laboratories) at room temperature for 45 minutes. The plates are washed and then incubated with 100 µL of 3,3', 5,5'-tetra-methylbenzidine. The absorbance at 450 nm is read on a SpectraMax® microplate reader. The half maximal effective concentration (EC50) is calculated using GraphPad Prism 7 software.

In experiments performed essentially as described above, Antibody 1 binds human CD226 with an EC50 of 0.1 nM.

Antibody 1 Binds to Cynomolgus Monkey CD226

The ability of the antibodies disclosed herein to bind to cell surface cynomolgus monkey CD226 can be measured using a flow cytometric assay. Cynomolgus monkey CD226 expressing stable cells are generated by transfecting Cyno-CD226 plasmid DNA into human HEK 293 cells (ATCC) using Fugene-6 reagent (Promega) according to the manufacturer's protocol. Stable cells are selected using 0.5 µg/mL puromycin in Dulbecoo's Modified Eagle's Medium containing 10% fetal bovine serum and 1% GlutaMAX™. For flow cytometry, confluent adherent cells are detached using Gibco® Cell Dissociation Buffer (Life Technologies), washed with complete media, then resuspend in FACS buffer (phosphate buffered saline containing 2.5% fetal bovine serum+1 mM EDTA) and then transferred into a 96 well V bottom plate at a density of $5 \times 10^4$ cells/well. Cells are stained for 30 minutes at room temperature with Antibody 1 or Control human IgG1 (prepared in FACS buffer starting at 100 µg/mL and serial diluted 1:3 with FACS buffer for a total of 7 concentrations).

After washing in FACS buffer, secondary antibody allophycocyanin (APC) conjugated goat anti-human IgG, F(ab')2 fragment specific antibody (Jackson ImmunoResearch Laboratories) is added at a 1:200 dilution and cells are incubated at room temperature for 30 minutes. Cells are washed and resuspended in FACS buffer. 7-amino-actinomycin D (7-AAD) viability staining solution (BD Biosciences) is added to each sample immediately before processing samples on a BD LSRFortessa X-20 cell analyzer. Flow cytometry data is analyzed using FlowJo® Software.

Median fluorescence intensity (MFI) ratio is calculated as the (MFI of Experimental antibody)/(MFI of the control IgG).

In experiments performed essentially as described above, Antibody 1 at a concentration of 0.14 µg/mL displays a higher MFI ratio of 2917.5 (11495/3.94).

Antibody 1 Binds to Human CD226 on the Cell Surface

The ability of the antibodies disclosed herein to bind to cell surface Human CD226 can be measured using a flow cytometric assay. Human CD226 expressing stable cells are generated by transfecting human-CD226 plasmid DNA into human HEK 293 cells (ATCC) using Fugene-6 reagent (Promega) according to the manufacturer's protocol. Stable cells are selected using 0.5 µg/mL puromycin in Dulbecoo's Modified Eagle's Medium containing 10% fetal bovine serum and 1% GlutaMAX™. For flow cytometry, confluent adherent cells are detached using Gibco® Cell Dissociation Buffer (Life Technologies), washed with complete media, then resuspend in FACS buffer (phosphate buffered saline containing 2.5% fetal bovine serum+1 mM EDTA) and then transferred into a 96 well V bottom plate at a density of $5 \times 10^4$ cells/well. Cells are stained for 30 minutes at room temperature with Antibody 1 or Control human IgG1 (prepared in FACS buffer starting at 100 µg/mL and serial diluted 1:3 with FACS buffer for a total of 10 concentrations).

After washing in FACS buffer, secondary antibody allophycocyanin (APC) conjugated goat anti-human IgG, F(ab')2 fragment specific antibody (Jackson ImmunoResearch Laboratories) is added at a 1:200 dilution and cells are incubated at room temperature for 30 minutes. Cells are washed and resuspended in FACS buffer. 7-amino-actinomycin D (7-AAD) viability staining solution (BD Biosciences) is added to each sample immediately before processing samples on a BD LSRFortessa X-20 cell analyzer. Flow cytometry data is analyzed using FlowJo® Software. Median fluorescence intensity (MFI) ratio is calculated as the (MFI of Experimental antibody)/(MFI of the control IgG).

In experiments performed essentially as described above, Antibody 1 at a concentration of 0.14 µg/mL displays a higher MFI ratio of 850.78 (7640/8.98).

Kinetics/Affinity Results for Antibody 1

A Biacore T200 instrument can be used to measure the kinetics of immobilized human CD226-Fc binding to Antibody 1. Recombinant human CD226-Fc fusion protein (R&D Systems) is covalently immobilized to a CM5 sensor chip via amine coupling (GE Healthcare). CD226 antibody testing is performed at a flow rate of 100 µL/min in HBS-EP+buffer. Samples are injected at various concentrations and measurements obtained at 25° C. The surface is regenerated after each sample injection with 10 mM Glycine-HCl pH 2.1 at flow rate of 10 µL/min for 30 seconds and then stabilized with buffer for 10 seconds. Sensorgrams of concentrations ranging from 1.95 nM to 1000 nM are evaluated using Biacore T200 software. The equilibrium dissociation constant (KD) or binding affinity constant is calculated from steady state fit. In experiments performed essentially as described above, Antibody 1 binds to human CD226 with the affinity constants illustrated in Table 2.

TABLE 2

| $K_D$ (nM) | $R_{max}$ | $Chi^2$ |
|---|---|---|
| 333.5 ± 23.5 | 35 ± 4.7 | 0.14 ± 0.03 |

NF-kappaB Luciferase Reporter Assay Activity of Antibody 1

The ability of the antibodies disclosed herein to activate NF-kappaB can be measured as follows. Double transient transfection of NF-kappaB luciferase reporter and pGL4.32 [luc2P/NF-kappaB-RE/Hygro] plasmids into HEK 293 cells is performed by plasmid DNAs using Lipofectamine™ 2000 Reagent (Life Technologies) according to the manufacturer's protocol in Dulbecoo's Modified Eagle's Medium containing 10% fetal bovine serum and 1% GlutaMAX™. The cells are cultured overnight at 37° C. and the next day cells are split into 96 well plate. Antibody 1 or control human IgG1 are diluted in medium 10-point 3-fold dilutions and added to the plate starting at 200 nM. Cells are then incubated with the antibodies for 18 h at 37° C. in 5% $CO_2$ and then processed using the ONE-Glo™ Luciferase Assay System (Promega™). Luminescence is measured using a SpectraMax® microplate reader. The half maximal effective concentration (EC50) is calculated using GraphPad Prism 7 software.

In experiments performed essentially as described above, Antibody 1 induces human CD226 mediated NF-kB reporter with an EC50 of 4.11 nM.

Antibody 1 Promotes T Cell-Derived Interferon-Gamma Production

The ability of the antibodies disclosed herein to promote T cell-derived interferon-gamma (IFN-gamma) production can be measured as follows. Human peripheral blood mononuclear cells (PBMCs) are isolated from whole blood or leukopacs by Ficoll density gradient centrifugation (Ficoll® Paque PLUS; GE Healthcare). CD8 T cells are isolated from PBMCs using a CD8 T cell isolation kit (Miltenyi) according to manufacturer's instructions and are resuspended in X Vivo-15 medium (Lonza) at a concentration of 0.75 million per mL. Antibody 1 or control human IgG1 are prepared by diluting in X Vivo-15 medium (Lonza) at 200 ug/mL. Anti-human CD3 antibody clone Hit3A (BD Biosciences) and anti-human CD28 antibody clone CD28.2 (BioLegend) are added to the CD8 T cell suspension at a concentration of 10 µg/mL and 2 µg/mL respectively. The cells are plated in a 96 well u-bottom plate at 100 µL per well followed by the antibodies at equal volume and incubated for 96 h at 37° C. in a humidified 5% CO2 incubator. Supernatants are collected and human IFN-gamma levels are measured using a R&D Systems® human IFN-gamma Quantikine® ELISA Kit. Briefly, sample supernatants and IFN-gamma standards are diluted in assay buffer and added to plates pre-coated with IFN-gamma capture antibody and incubated for 2 h at room temperature. After washing, 200 µL of IFN-gamma detection antibody is added and incubated for 2 hr at room temperature. After washing, plates are developed by adding 200 µL substrate solution for 10 minutes followed by 50 µL stop solution, and the signal is measured at 450 nM with SpectraMax® microplate reader. Data analysis is performed using SoftMax Pro software and GraphPad Prism (GraphPad Software).

In experiments performed essentially as described above, Antibody 1 enhances the sub-optimal activation of human PBMCs by CD3/CD28 co-stimulation as measured by IFN-gamma cytokine production. In this regard, treatment with Antibody 1 at 100 µg/mL results in a 1.6-fold increase in the production of IFN-gamma over control IgG treatment.

Antitumor Efficacy of Antibody 1 in an Established Tumor Model

The HCC827 human non-small cell lung cancer (ATCC) tumor cell line is maintained in its respective media and harvested for implantation. Tumor cells ($1 \times 10^7$ cells per mouse) are injected subcutaneously into the right flank of female NOD/SCID Gamma (NSG) mice at 7 weeks of age (Jackson Laboratories). When tumors reach approximately 250 mm³ to 350 mm³ in size, mice are randomized into groups of 5 to 8. Human expanded T cells are generated by stimulating naïve human PBMCs with Dynabeads® Human T-expander CD3/CD28 beads (Thermo Fisher Scientific) for 9 to 10 days and banked. Human PBMCs (NY Blood Center) are prepared by centrifugation over Ficoll® Paque PLUS in SepMate tubes (STEMCELL Technologies) and banked. Expanded T cells are thawed and 2.5×10⁶ cells are injected into the mice. As a control, tumor cells alone are implanted with no T cells in some mice. Treatment starts at either Day 0 or Day 1. Treatment groups include control IgG and Antibody 1. Animals are dosed via intraperitoneal injection at 10 mg/kg of antibody once weekly for 4 weeks. Body weight (BW) is recorded twice a week and the percent change in BW is calculated using the formula: (BW on observation day−BW on initial day)/BW initial day×100%. Tumor volumes are measured twice per week using electronic calipers. Tumor volume is calculated using the formula: Tumor Volume (mm³)=π/6*Length*Width². The % T/C is calculated using the formula 100×ΔT/ΔC if ΔT>0 of the geometric mean values. ΔT=mean tumor volume of the drug-treated group on the observation day of the study−mean tumor volume of the drug-treated group on initial day of dosing; ΔC=mean tumor volume of the control group on the observation day of the study−mean tumor volume of the control group on initial day of dosing. Statistical analysis of tumor volume data is performed by two-way repeated measures analysis of variance by time and treatment using the MIXED procedures in SAS software (Version 9.2).

In experiments performed essentially as described above, mice treated with Antibody 1 demonstrated significant tumor growth inhibition (T/C %=56.7; P<0.01).

```
Amino Acid and Nucleotide Sequences
(Antibody 1 HCDR1)
                                                         SEQ ID NO: 1
AASGFTFSSYAMS (Antibody 1 HCDR2)
                                                         SEQ ID NO: 2
AISGSGGSTYYADSVKG (Antibody 1 HCDR3)
                                                         SEQ ID NO: 3
ARDRWELHDAFDI (Antibody 1 LCDR1)
                                                         SEQ ID NO: 4
RASQSISSYLN (Antibody 1 LCDR2)
                                                         SEQ ID NO: 5
YRASTLQS (Antibody 1 LCDR3)
                                                         SEQ ID NO: 6
QQSYSTPDT (Antibody 1 HCVR)
                                                         SEQ ID NO: 7
EVQLLESGGGLVQPGGSLRLSCAASGFTFSSYAMSWVRQAPGKGLEWVSAISGS

GGSTYYADSVKGRFTISRDNSKNTLYLQMNSLRAEDTAVYYCARDRWELHDAF

DIWGQGTMVTVSS (Antibody 1 LCVR)
                                                         SEQ ID NO: 8
VIWTQSPSSLSASVGDRVTITCRASQSISSYLNWYQQKPGKAPRLLIYRASTLQS

GVPSRFSGDGSGTHFTLTISSLQPEDFATYYCQQSYSTPDTFGQGTKVEIK (Antibody 1 HC)
                                                         SEQ ID NO: 9
EVQLLESGGGLVQPGGSLRLSCAASGFTFSSYAMSWVRQAPGKGLEWVSAISGS

GGSTYYADSVKGRFTISRDNSKNTLYLQMNSLRAEDTAVYYCARDRWELHDAF

DIWGQGTMVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSNTKVDKR

VEPKSCDKTHTCPPCPAPEAEGAPSVFLFPPKPKDTLMISRTPEVTCVVVDVSHED

PEVKFNWYVDGVEVHNAKTKPREEQYNSTYRVVSVLTVLHQDWLNGKEYKCK

VSNKALPSSIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVMHEAL

HNHYTQKSLSLSPGK
```

(Antibody 1 LC)

SEQ ID NO: 10

VIWMTQSPSSLSASVGDRVTITCRASQSISSYLNWYQQKPGKAPRLLIYRASTLQS
GVPSRFSGDGSGTHFTLTISSLQPEDFATYYCQQSYSTPDTFGQGTKVEIKRTVAA
PSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (Antibody 1 HC DNA)

SEQ ID NO: 11 gaggtgcagctgttggagtctgggggaggcttggtacagcctggggggtccctgagactctcctgtgcagcctctggattcacct
ttagcagctatgccatgagctgggtccgccaggctccagggaaggggctggagtgggtctcagctattagtggtagtggtggta
gcacatactacgcagactccgtgaagggccggttcaccatctccagagacaattccaagaacacgctgtatctgcaaatgaaca
gcctgagagccgaggacacggccgtatattactgtgcgagagatcggtgggagcttcatgatgcttttgatatctggggccaagg
gacaatggtcaccgtctcttcagctagcaccaagggcccatcggtcttccccctggcaccctcctccaagagcacctctggggg
cacagcggccctgggctgcctggtcaaggactacttccccgaaccggtgacggtgtcgtggaactcaggcgcactgaccagc
ggcgtgcacaccttcccggctgtcctacagtcctcaggactctactccctcagcagcgtggtgaccgtgccctccagcagcttgg
gcacccagacctacatctgcaacgtgaatcacaagcccagcaacaccaaggtggacaagagagttgagcccaaatcttgtgac
aaaactcacacatgcccaccgtgcccagcacctgaagccgaggggggcaccgtcagtcttcctcttccccccaaaacccaagga
caccctcatgatctcccggacccctgaggtcacatgcgtggtggtggacgtgagccacgaagaccctgaggtcaagttcaactg
gtatgtggacggcgtggaggtgcataatgccaagacaaagccgcgggaggagcagtacaacagcacgtaccgtgtggtcagc
gtcctcaccgtcctgcaccaagactggctgaatggcaaggagtacaagtgcaaggtctccaacaaagcccctcccatcctccatc
gagaaaaccatctccaaagccaaagggcagccccgagaaccacaggtgtacaccctgcccccatcccgggaggagatgacc
aagaaccaagtcagcctgacctgcctggtcaaaggcttctatcccagcgacatcgccgtggagtgggagagcaatgggcagcc
ggagaacaactacaagaccacgcctcccgtgctggactccgacggctccttcttcctctattccaagctcaccgtggacaagagc
aggtggcagcaggggaacgtcttctcatgctccgtgatgcatgaggctctgcacaaccactacacgcagaagagcctctccctg
tctccgggcaaa (Antibody 1 LC DNA)

SEQ ID NO: 12 gtcatctggatgacccagtctccatcctccctgtctgcatctgtaggagacagagtcaccatcacttgccgggcaagtcagagcat
tagcagctatttaaattggtatcagcagaaaccagggaaagcccctaggctcctgatctaccgtgcatccactttacaaagtgggg
tcccatcaaggttcagtggcgatggatctggaacacatttcactctcaccatcagcagcctccagcctgaagattttgcaacttact
actgtcaacagagttacagtaccccccgacacttttggccaggggaccaaggtggaaatcaaacgaactgtggctgcaccatctgt
cttcatcttcccgccatctgatgagcagttgaaatctggaactgcctctgttgtgtgcctgctgaataacttctatcccagagaggcc
aaagtacagtggaaggtggataacgcccctccaatcgggtaactcccaggagagtgtcacagagcaggacagcaaggacagc
acctacagcctcagcagcaccctgacgctgagcaaagcagactacgagaaacacaaagtctacgcctgcgaagtcacccatca
gggcctgagctcgcccgtcacaaagagatcaacaggggagagtgt (Human CD226)

SEQ ID NO: 13

MDYPTLLLALLHVYRALCEEVLWHTSVPFAENMSLECVYPSMGILTQVEWFKIG
TQQDSIAIFSPTHGMVIRKPYAERVYFLNSTMASNNMTLFFRNASEDDVGYYSCS
LYTYPQGTWQKVIQVVQSDSFEAAVPSNSHIVSEPGKNVTLTCQPQMTWPVQAV
RWEKIQPRQIDLLTYCNLVHGRNFTSKFPRQIVSNCSHGRWSVIVIPDVTVSDSGL
YRCYLQASAGENETFVMRLTVAEGKTDNQYTLFVAGGTVLLLLFVISITTIIVIFL
NRRRRRERRDLFTESWDTQKAPNNYRSPISTSQPTNQSMDDTREDIYVNYPTFSR
RPKTRV (Human CD226-Extracellular Domain-Fc)    SEQ ID NO: 14

EEVLWHTSVPFAENMSLECVYPSMGILTQVEWFKIGTQQDSIAIFSPTHGMVIRKP

YAERVYFLNSTMASNNMTLFFRNASEDDVGYYSCSLYTYPQGTWQKVIQVVQS

DSFEAAVPSNSHIVSEPGKNVTLTCQPQMTWPVQAVRWEKIQPRQIDLLTYCNLV

HGRNFTSKFPRQIVSNCSHGRWSVIVIPDVTVSDSGLYRCYLQASAGENETFVMR

LTVAEGKTDNHIEGRMDPKSCDKTHTCPPCPAPELLGGPSVFLFPPKPKDTLMISR

TPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRW

QQGNVFSCSVMHEALHNHYTQKSLSLSPGK

---

I claim:

1. An anti-human CD226 antibody, comprising an HCDR1 having the amino acid sequence of SEQ ID NO: 1, an HCDR2 having the amino acid sequence of SEQ ID NO: 2, an HCDR3 having the amino acid sequence of SEQ ID NO: 3, an LCDR1 having the amino acid sequence of SEQ ID NO: 4, an LCDR2 having the amino acid sequence of SEQ ID NO: 5, and an LCDR3 having the amino acid sequence of SEQ ID NO: 6.

2. The anti-human CD226 antibody of claim 1, comprising an HCVR having the amino acid sequence of SEQ ID NO: 7 and an LCVR having the amino acid sequence of SEQ ID NO: 8.

3. The anti-human CD226 antibody of claim 1, comprising an HC having the amino acid sequence of SEQ ID NO: 9, and an LC having the amino acid sequence of SEQ ID NO: 10.

4. The anti-human CD226 antibody of claim 1, consisting of two HCs having the amino acid sequence of SEQ ID NO: 9, and two LCs having the amino acid sequence of SEQ ID NO: 10.

5. A pharmaceutical composition, comprising the anti-human CD226 antibody of 3, and an acceptable carrier, diluent, or excipient.

6. A DNA molecule comprising a polynucleotide having the sequence of SEQ ID NO: 11, SEQ ID NO: 12, or SEQ ID NOS: 11 and 12.

7. A method of treating a solid tumor cancer, comprising administering to a patient in need thereof, an effective amount of the anti-human CD226 antibody of 3, wherein the solid tumor cancer is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, soft tissue sarcoma, gastric cancer, testicular cancer, thyroid cancer, uterine cancer or urothelial cancer.

* * * * *

UNITED STATES PATENT AND TRADEMARK OFFICE
CERTIFICATE OF CORRECTION

PATENT NO. : 11,440,959 B2
APPLICATION NO. : 16/500947
DATED : September 13, 2022
INVENTOR(S) : Naresh Kumar It is certified that error appears in the above-identified patent and that said Letters Patent is hereby corrected as shown below:

In the Claims

In Column 36, Line 28, in Claim 5, delete "3," and insert -- claim 3, --.

In Column 36, Line 36, in Claim 7, delete "3," and insert -- claim 3, --.

Signed and Sealed this
Fifteenth Day of November, 2022

Katherine Kelly Vidal
*Director of the United States Patent and Trademark Office*